United States Patent [19]
Inoue et al.

[11] Patent Number: 4,834,907
[45] Date of Patent: May 30, 1989

[54] LIQUID CRYSTALLINE ESTER COMPOUNDS AND MIXTURES THEREOF

[75] Inventors: Hiromichi Inoue; Shinichi Saito; Kazutoshi Miyazawa; Takashi Inukai; Kanetsugu Terashima, all of Yokohama, Japan

[73] Assignee: Chisso Corporation, Osaka, Japan

[21] Appl. No.: 4,815

[22] Filed: Jan. 8, 1987

Related U.S. Application Data

[63] Continuation of Ser. No. 688,147, Dec. 31, 1984, abandoned.

[30] Foreign Application Priority Data

Jun. 11, 1984 [JP] Japan .................. 59-119590

[51] Int. Cl.$^4$ .............. C09K 19/12; C09K 19/20; C09K 19/52; G02F 1/13
[52] U.S. Cl. .................. 252/299.65; 252/299.01; 252/299.67; 252/299.66; 558/270; 558/271; 560/59; 560/66; 560/73; 560/108; 560/141; 350/350 S
[58] Field of Search ............ 252/299.01, 299.65, 252/299.67; 560/59, 61, 73, 66; 558/270, 271; 350/350 S

[56] References Cited

U.S. PATENT DOCUMENTS

| | | | |
|---|---|---|---|
| 4,065,489 | 12/1977 | Steinstrasser | 252/299.65 |
| 4,083,797 | 4/1978 | Oh | 252/299.66 |
| 4,149,413 | 4/1979 | Gray et al. | 252/299.65 |
| 4,195,916 | 4/1980 | Coates et al. | 252/299.65 |
| 4,257,911 | 3/1981 | Gray et al. | 252/299.65 |
| 4,576,732 | 3/1986 | Isogai et al. | 252/299.65 |
| 4,596,667 | 6/1986 | Inukai et al. | 252/299.65 |
| 4,613,209 | 9/1986 | Goodby et al. | 252/299.67 |
| 4,614,609 | 9/1986 | Inoue et al. | 252/299.66 |
| 4,647,398 | 3/1987 | Saito et al. | 252/299.65 |
| 4,689,176 | 8/1987 | Inoue et al. | 252/299.65 |
| 4,710,585 | 12/1987 | Taguchi et al. | 252/299.65 |
| 4,728,458 | 3/1988 | Higuchi et al. | 252/299.65 |

FOREIGN PATENT DOCUMENTS

| | | | |
|---|---|---|---|
| 0115693 | 8/1984 | European Pat. Off. | 252/299.67 |
| 0136725 | 4/1985 | European Pat. Off. | 252/299.67 |
| 53-88677 | 8/1978 | Japan | 252/299.67 |

OTHER PUBLICATIONS

Gray et al, Mol. Cryst. Liq. Cryst., vol. 34 Letters, pp. 211-217 (1977).
Goodby & Leslie, Liquid Crystals and Ordered Fluids, vol. 4, 1984, pp. 1-32.
Gray & McDonnell, Mol. Cryst. Liq. Cryst., 1976, 37, pp. 189-211.
Gray & Goodby, Mol. Cryst. Liq. Cryst., 1976, 37, pp. 157-188.

Primary Examiner—Teddy S. Gron
Assistant Examiner—J. E. Thomas
Attorney, Agent, or Firm—Wenderoth, Lind & Ponack

[57] ABSTRACT

Novel chiral smectic liquid crystalline ester compounds having a superior stability and exhibiting a high response rate when used in the form of display elements and chiral smectic mixtures containing at least one of these compounds are provided, which compounds are expressed by the formula

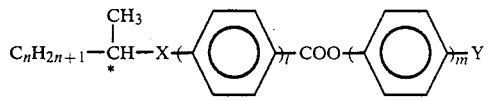

wherein n is an integer of 2 to 16; l is 0, 1 or 2; m is 1 or 2 under the condition of $1+m \geq 2$; X represents methylene group —CH$_2$— or single bond when l is zero, methylene group —CH$_2$— or ether linkage —O— when l=1 or ether linkage —O— when l=2; and Y represents R, OR, —COR, —OCOR, —OCOOR or —COOR wherein R throughout represents an alkyl group of 1 to 18 carbon atoms; and asterisk * shows an optically active carbon atom.

5 Claims, No Drawings

LIQUID CRYSTALLINE ESTER COMPOUNDS AND MIXTURES THEREOF

This application is a continuation of now abandoned application Ser. No. 688,147, filed Dec. 31, 1984.

BACKGROUND OF THE INVENTION

1. Field of the Invention

This invention relates to novel liquid crystalline compounds and liquid crystalline mixtures containing the same, and more particularly, it relates to chiral smectic compounds which have a high response rate and are superior as a ferroelectric liquid crystalline material, and also to chiral smectic mixtures containing the same.

2. Description of the Prior Art

Twisted nematic (TN) type display mode has currently been most widely employed as liquid crystal display elements, but it is inferior in the response rate as compared with emissive type display elements such as electroluminescence, plasma display, etc., and various attempts for overcoming this drawback have been made, but, nevertheless, it seems that its improvement to a large extent has not been realized. Thus, various liquid crystal display equipments based on different principles in place of TN type display elements have been attempted, and as one of them, there is a display mode utilizing ferroelectric liquid crystals (N. A. Clark and S. T. Layerwall, Applied Phys. lett., 36,899 (1980)). This mode utilizes the chiral smectic C phase (hereinafter abbreviated to SC* phase) or chiral smectic H phase (hereinafter abbreviated to SH* phase) of ferroelectric liquid crystals. As such ferroelectric liquid crystal compounds, the following compounds (1) to (4) have been known up to the present (ph. Martino Lagarde, J. de Physique, 37, C3-129 (1976)):

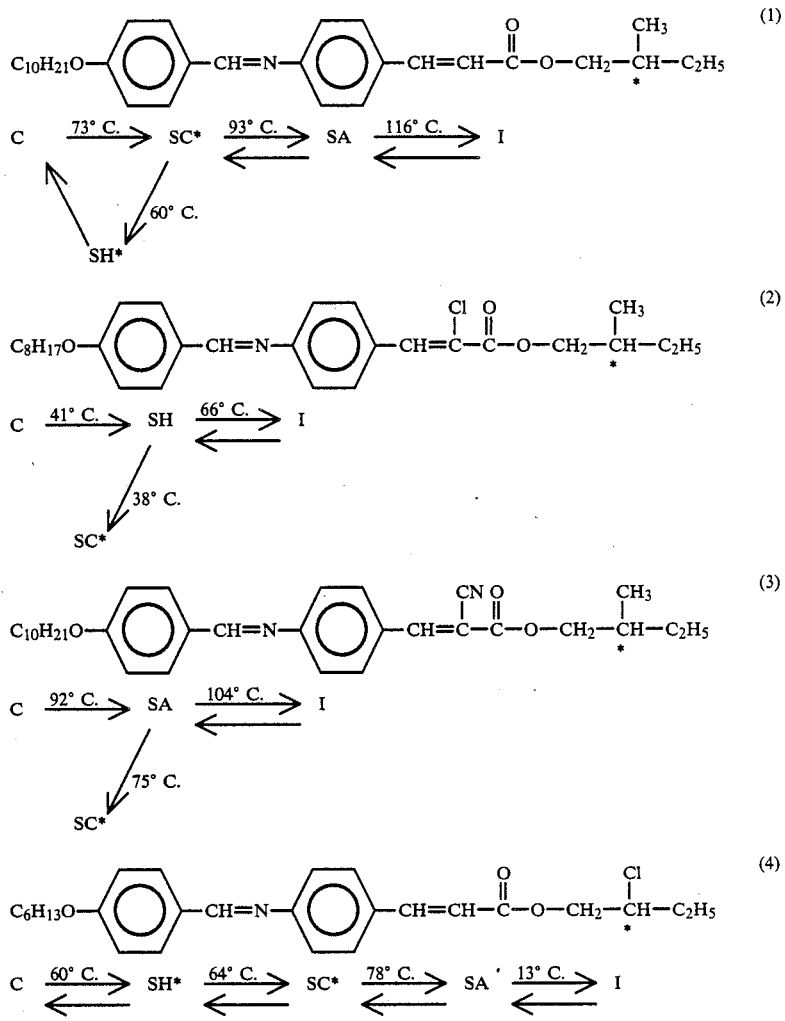

In the foregoing, C represents crystalline phase; SA, smectic A phase; I, isotropic liquid phase; SC* and SH*, as described above; and "*", optically active carbon atom.

Further, as ferroelectric liquid crystal compounds, the following two compounds (5) and (6) have also been known:

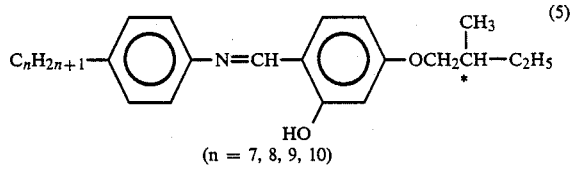

(n = 7, 8, 9, 10)

-continued

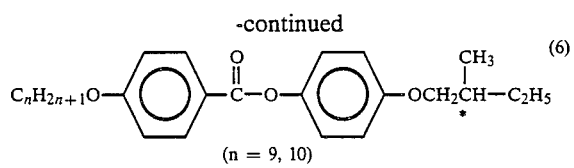

(n = 9, 10)

(B. I. Ostrovski, A. Z. Rabinovich, A. S. Sonin, E. L. Sorkin, B. A. Strukov, and S. T. Taraskin; Ferroelectrics, 24, 309 (1980)).

Among these compounds, since the compounds (1) to (4) have C=C double bond and azomethine group, they have drawbacks of being inferior in light resistance and water resistance. The compounds (5) also have azomethine group and hence are inferior in water resistance. The compounds (6) do not have these bonds and hence are superior in stability, but the above Ostrovski et al's article discloses as to their phase transition temperatures, only that the upper limit temperatures of SC* phase are 324.8° K. (in the case of n=9) and 326.2° K. (in the case of n=10), but nothing is disclosed therein as to other liquid crystalline phase modifications.

The present inventors have investigated and studied various compounds including the above compounds (1) to (6) and as a result, have found ferroelectric liquid crystal compounds having a superior stability.

A group of these compounds is those previously filed as U.S. Ser. No. 568,060 (Jan. 4, 1984) U.S. Pat. No. 4,596,667 and expressed by the following formula:

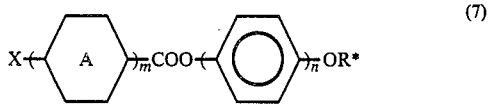

wherein

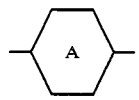

represents 1,4-phenylene group

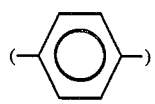

or 1,4-trans-cyclohexane group

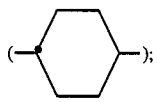

R*, an optically active alkyl group; m=0, 1 or 2; n=1 or 2; X, a linear chain or branched alkyl group or alkoxy group, each having 1 to 18 carbon atoms; and when

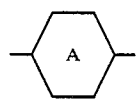

represents

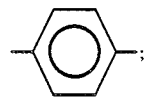

m=1; and n=1, X represents a linear chain or branched alkyl group having 1 to 18 carbon atoms or a linear chain alkoxy group having 11 to 18 carbon atoms.

The compounds of the present invention are also used for the same object as that of the above compounds.

SUMMARY OF THE INVENTION

The present invention resides in:

Liquid crystalline ester compounds expressed by the formula (I)

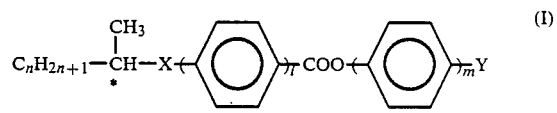

wherein n represents an integer of 2 to 16; l represents 0, 1 or 2 and m represents 1 or 2 under the condition of $1+m \geq 2$; X represents methylene group —$CH_2$— or single bond when l=0, methylene group —$CH_2$13 or ether linkage —O— when l=1, or ether linkage —O— when l=2, and Y represents R, OR, —COR, OCOR, —OCOOR, or —COOR wherein R throughout means an alkyl group of 1 to 18 carbon atoms; and asterisk * shows an optically active carbon atom;

and chiral smectic liquid crystal compositions containing at least one of these compounds.

DESCRIPTION OF THE PREFERRED EMBODIMENTS

Compounds of the formula (I) wherein X represents methylene group, l represents 0, and m represents 2 are expressed by the following formula (II):

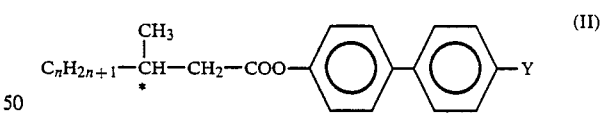

Table 1 shows examples of the esters of the formula (II) with n=2 and their liquid crystalline phase transition points.

TABLE 1

| Sample No. | Y in formula (II) | Phase transition points (°C.) | | | | | |
|---|---|---|---|---|---|---|---|
| | | C | SX | SH* | SC* | SA | I |
| 1 | $C_8H_{17}O$— | · 56.2 | · 91.8 | — | · 94.8 | — | · |
| 2 | $C_{10}H_{21}O$— | · 65.7 | · — | (· 63.4) | · 83.9 | · 99.8 | · |
| 3 | $C_{14}H_{29}O$— | · 77.5 | · — | — | · 83.4 | · 89.5 | · |
| 4 | $C_7H_{15}$ | · 40.4 | · 68.7 | — | — | — | · |

Compounds of the formula (I) wherein X represents single bond, l represents 0, and m represents 2 are expressed by the following formula (III):

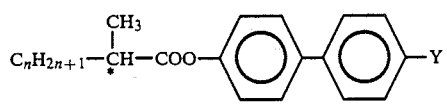   (III)

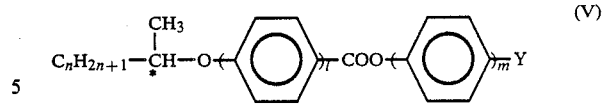   (V)

Table 2 shows examples of the compound of formula (III), with n=2, and their phase transition points.

Table 4 shows example of the compound of the formula (V) and their phase transition points.

TABLE 4

| Sample No. | Y in formula (V) | n | l | m | Phase transition points (°C.) C | SC* | SA | Ch | I |
|---|---|---|---|---|---|---|---|---|---|
| 13 | $C_7H_{15}$ | 6 | 2 | 1 | · 51.0 | · 70.4 | · 80.8 | · 95.5 | · |
| 14 | $C_8H_{17}$ | 6 | 2 | 1 | · 55.0 | · 71.5 | · 83.6 | · 92.3 | · |
| 15 | $C_9H_{19}$ | 6 | 2 | 1 | · 52.2 | · 74.0 | · 80.6 | · 91.7 | · |
| 16 | $OC_5H_{11}$ | 6 | 2 | 1 | · 76.0 | · 93.5 | — | · 121.6 | · |
| 17 | $OC_7H_{15}$ | 6 | 2 | 1 | · 72.0 | · 100.2 | — | · 123.5 | · |
| 18 | $OC_8H_{17}$ | 6 | 2 | 1 | · 78.7 | · 103.3 | — | · 120.8 | · |
| 19 | $OC_9H_{19}$ | 6 | 2 | 1 | · 78.0 | · 104.2 | | · 118.2 | · |
| 20 | $OC_{11}H_{23}$ | 6 | 2 | 1 | · 86.0 | · 105.2 | | · 115.8 | · |
| 21 | $OC_{12}H_{25}$ | 6 | 2 | 1 | · 81.0 | · 105.3 | | · 115.0 | · |
| 22 | $-OCOOC_8H_{17}$ | 6 | 2 | 1 | · 65.8 | · 83.0 | | · 114.6 | · |
| 23 | $-COOC_6H_{13}$ | 6 | 2 | 1 | · 68.2 | (· 46.0) | · 94.7 | — | · |
| 24 | $C_7H_{15}$ | 3 | 1 | 2 | · 93.2 | — | — | · 109.9 | · |
| 25 | $OC_6H_{13}$ | 3 | 1 | 2 | · 98.8 | (· 86.2) | — | · 143.3 | · |
| 26 | $OC_8H_{17}$ | 3 | 1 | 2 | · 92.0 | · 95.2 | — | · 137.0 | · |
| 27 | $OC_9H_{19}$ | 3 | 1 | 2 | · 91.2 | · 97.7 | — | · 132.2 | · |
| 28 | $OC_{10}H_{21}$ | 3 | 1 | 2 | · 85.5 | · 99.1 | — | · 128.3 | · |
| 29 | $OC_{11}H_{23}$ | 3 | 1 | 2 | · 76.6 | · 98.0 | — | · 123.0 | · |
| 30 | $O.COOC_8H_{17}$ | 3 | 1 | 2 | · 56.0 | · 65.9 | — | · 126.6 | · |
| 31 | $OC_8H_{17}$ | 3 | 2 | 1 | · 71.8 | · 89.8 | — | · 137.4 | · |
| 32 | $OC_6H_{13}$ | 6 | 1 | 2 | · 74.0 | · 84.5 | — | · 140.5 | · |
| 33 | $OC_8H_{17}$ | 6 | 1 | 2 | · 78.2 | · 92.0 | — | · 122.3 | · |
| 34 | $OC_9H_{19}$ | 6 | 1 | 2 | · 78.9 | · 100.1 | — | · 118.1 | · |
| 35 | $OC_{10}H_{21}$ | 6 | 1 | 2 | · 77.8 | · 103.0 | — | · 117.1 | · |
| 36 | $OCOOC_8H_{17}$ | 6 | 1 | 2 | · 61.3 | · 81.5 | — | · 108.2 | · |
| 37 | $OC_5H_{11}$ | 6 | 1 | 1 | · 27.7 | — | — | — | · |
| 38 | $OC_8H_{17}$ | 6 | 1 | 1 | · 18 | — | — | — | · |

TABLE 2

| Sample No. | Y in Formula (III) | Phase transition points (°C.) C | SX | SH* | SC* | SA | I |
|---|---|---|---|---|---|---|---|
| 5 | $C_8H_{17}O-$ | · 69.4 | — | — | · 84.4 | — | · |
| 6 | $C_{10}H_{21}O-$ | · 74.8 | — | · 75.8 | · 79.4 | · 83.2 | · |
| 7 | $C_{14}H_{29}O-$ | · 84.0 | — | — | — | (· 81.4) | · |
| 8 | $C_7H_{15}$ | · 28.5 | · 57.3 | — | — | — | · |

Compounds of the formula (I) wherein X represents methylene group, l represents 1 and m represents 2 are expressed by the formula (IV):

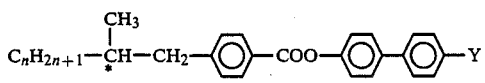   (IV)

Table 3 shows examples of the esters of the formula (IV), and their phase transition points.

TABLE 3

| Sample No. | In formula (IV) Y | Phase transition points (°C.) C | SX | SC* | SA | Ch | I |
|---|---|---|---|---|---|---|---|
| 9 | $C_8H_{17}O-$ | · 58.5 | · 83.4 | — | — | · 159.6 | · |
| 10 | $C_{10}H_{21}O-$ | · 49.8 | — | · 63.9 | · 121.8 | · 143.6 | · |
| 11 | $C_{14}H_{29}O-$ | · 80.8 | — | · 93.1 | · 130.8 | — | · |
| 12 | $C_7H_{15}$ | · 98.9 | — | (· 91.2) | · 152.0 | — | · |

Compounds of the formula (I) wherein X represents ether linkage —O—, and l and m represent 1 or 2 are expressed by the formula (V)

As to the compounds of the formula (I), some exhibit both cholesteric phase and smectic phase in a definite temperature range, while the others do not exhibit cholesteric phase, but exhibit smectic phase, alone, in the range. However, the compounds have a main specific feature in that SC* phase is present in the smectic phase.

Among the compounds of the formula (I) of the present invention, a group of the compounds expressed by the formula (V) have a further merit that they have a large value of spontaneous polarization (Ps) amounting to 40~90 nC/cm² (monocoulomb per square centimeter), as shown in the following Table 5:

TABLE 5

| Sample No. | Ps (nC/cm²)[1] |
|---|---|
| 26 | 46 |
| 27 | 38 |
| 29 | 30 |
| 31 | 68 |
| 33 | 46 |
| 34 | 50 |
| 35 | 43 |

[1]Values measured at a temperature lower by 20° C· than the upper limit temperature of SC* phase When SC* liquid crystal compositions are formed, it is possible to form them from a plurality of compounds of the formula (I), alone, and it is also possible to prepare liquid crystal compositions exhibiting SC* phase, by mixing compounds of the formula (I) with other smectic liquid crystals.

When the light switching effect of the SC* phase is applied to display elements, the resulting display elements have the following three superior specific features:

The first specific feature is that the elements reply at a very high rate and the response times are 1/100 or less of those of display elements according to the usual TN display mode.

The second specific feature is that the elements have a memory effect; hence multiplex drive is easy in combination of this effect with the above-mentioned high rate response properties.

The third specific feature is that gray scale in TN display mode is attained by controlling the impressed voltage applied to display elements, but this is accompanied with difficult problems of the temperature dependency of threshold voltage value and the voltage dependency of response rate. However, in the case where the light switching effect of SC* phase is applied to the display elements, it is possible to easily attain the gray scale by controlling the switching time of polarity; hence the display elements are very suitable for graphic display.

As for the display modes, the following two may be considered:

one mode is of birefringence type using two pieces of polarizers and another is of guest-host type using dichoric dyestuffs. Since SC* phase has a spontaneous polarization, molecules reverse around the helical axis thereof as a revolving axis by reversing the polarity of impressed voltage. A liquid crystal composition having SC* phase is filled in a liquid crystal display cell subjected to an aligning treatment so that liquid crystal molecules can align in parallel to the surface of electrodes, followed by placing the liquid crystal cell between two pieces of polarizers arranged so that the director of the liquid crystal molecules can be parallel to the polarization plane on another side, impressing a voltage and reversing the polarity to be thereby able to obtain a bright field and a dark field (determined by the opposed angles of polarizers). On the other hand, in the case where display elements are operated in guest-host mode, it is possible to obtain bright field and colored field (determined by the arrangement of polarization pieces) by reversing the polarity of impressed voltage.

In general, it is difficult to align liquid crystal molecules in smectic state in parallel to the wall surface of glass; hence liquid crystal molecules have been aligned by cooling them very slowly (e.g. $1° \sim 2°$ C./hr) initially starting from their isotropic liquid, in a magnetic field of several tens Kilogauss or more, but in the case of liquid crystal substances having cholesteric phase, the substances are cooled at a cooling rate of $1°$ C./min. under impression of a direct current voltage of 50 to 100 V in place of magnetic field, whereby it is possible to easily obtain a monodomain state where liquid crystal molecules are uniformly aligned.

Compounds of the formula (I) also have an optically active carbon atom; hence when they are added to nematic liquid crystals, they have a performance of having a twisted structure induced in the mixtures. Nematic liquid crystals having a twisted structure, i.e. chiral nematic liquid crystals, form no reverse domain (striped pattern); hence it is possible to use the compounds of the formula (I) as an agent for preventing reverse domain. Compounds particularly suitable for such an application field are those which by themselves exhibit cholesteric phase, and examples thereof are compounds of the formula (V) above.

When these compounds are added to nematic liquid crystals in an amount of about 0.05 to 3% by weight based on the latter, a twisting force in a definite direction is imparted to molecules so that the resulting nematic liquid crystals are free from the reverse domain.

In addition, racemi-form compounds corresponding to the compounds of the formula (I) are also liquid crystals exhibiting nearly the same phase transition points as those of the optically active form compounds of the formula (I), but they exhibit SC phase in place of SC* phase and SH phase in place of SH* phase, and when added to the optically active form compounds of the formula (I), they can be used for adjusting the chiral smectic pitch thereof. These racemi-form compounds can be prepared in the same manner as in the case of the optically active form compounds as mentioned later, if racemi-form raw materials are used therefor.

In addition, among optically active 2-alkanols as raw material, S(+)-2-octanol and R(−)-2-octanol are readily commercially available, but other optically active 2-alkanols are unsuitable for use in a large quantity due to their high cost. Thus, the present inventors subjected certain racemi-form 2-alkanols to optical resolution according to the method described in a literature (R. H. Pickard et al, J. Chem. Soc., 99, 45 (1911), and used the resulting optically active alkanols as raw material. By using these alkanols, it is possible to obtain various substances having different n values in the formula (V). Change in the liquid crystal phase transition temperature depending on the chain length of optically active groups is slight; hence it has no particular advantage to use as raw material, optically active 2-alkanols other than most readily commercially available 2-octanols. However, as to the upper limit temperature of SC* phase (i.e. SC*-Ch point) which is practically important, a tendency is observed that the longer the chain length, the higher the temperature although the increase is slight. This is shown in the following Table 6:

TABLE 6

| | SC*—Ch point (°C.) of compounds of the formula (V) | | | | |
|---|---|---|---|---|---|
| | l = 2, m = 1 | | | l = 1, m = 2 | |
| | Y | | | | |
| n | —OC$_8$H$_{17}$ | —OC$_{10}$H$_{21}$ | —OC$_{12}$H$_{25}$ | —OC$_9$H$_{19}$ | —OCOOC$_8$H$_{17}$ |
| 3 | 89.8 | 97.5 | 96.0 | 97.7 | 65.9 |
| 4 | 93.0 | 94.8 | 96.4 | 95.8 | 70.5 |
| 5 | 100.2 | — | — | 98.5 | 77.2 |
| 6 | 100.3 | 106.8 | 105.3 | 102.6 | 81.5 |

Preparation of the compounds of the present invention will be described below.

The compounds of the formula (I) are most preferably prepared by reacting an optically active carboxylic acid chloride with a p-substituted phenol or a 4-hydroxy-4'-substituted biphenyl in a basic solvent such as pyridine.

4-Alkyloxy-4'-hydroxybiphenyls among 4-hydroxy-4'-substituted biphenyls as one of the raw materials may be prepared according to the following steps:

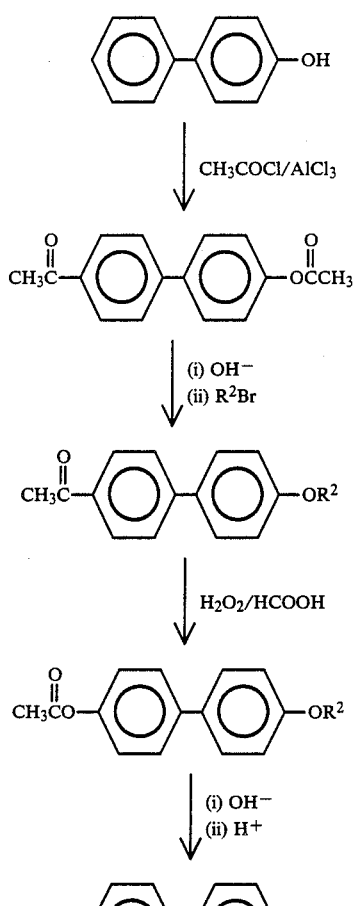

In the above figure, R² represents an alkyl group of 1~18 carbon atoms.

In the above steps, acetyl chloride is reacted with hydroxybiphenyl in the presence of anhydrous aluminum chloride in an amount of twice the number of mols of the latter compound to prepare 4-acetyloxy-4'-acetylbiphenyl, which is then reacted with an alkylbromide in the presence of KOH to prepare a 4-acetyl-4'-alkyloxybiphenyl, which is further reacted with hydrogen peroxide in formic acid to prepare a 4-acetyloxy-4'-alkyloxybiphenyl, which is then hydrolyzed with an alkali, followed by adding an acid to obtain the objective 4-alkyloxy-4'-hydroxybiphenyl.

4-Alkyl-4'-hydroxybiphenyls among 4-hydroxy-4'-substituted biphenyls may be prepared according to the following steps:

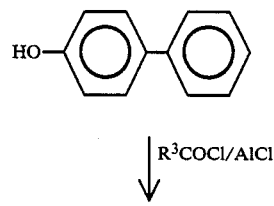

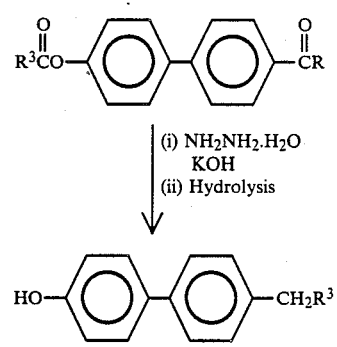

In the above figure, R³ represents an alkyl group having 1 to 17 carbon atoms.

In the above steps, an alkylcarboxylic acid chloride is reacted with hydroxybiphenyl in the presence of anhydrous aluminum chloride to prepare a 4-acyl-4'-acyloxybiphenyl, which is then subjected to Wolff-Kischner reduction and further hydrolyzed to prepare a 4-alkyl-4'-hydroxybiphenyl.

Further, optically active carboxylic acid chlorides as a counterpart raw material include

| | |
|---|---|
| $\underset{*}{C_nH_{2n+1}}\overset{CH_3}{\underset{|}{C}H}COCl$ | (α-methylalkanoyl chlorides) |
| $\underset{*}{C_nH_{2n+1}}\overset{CH_3}{\underset{|}{C}H}CH_2COCl$ | (β-methylalkanoyl chlorides) |
| $C_nH_{2n+1}\overset{CH_3}{\underset{*}{\underset{|}{C}H}}CH_2-\underset{}{\bigcirc}-COCl$ | (p-(2-methylalkyl)-benzoyl chlorides) |
| $C_nH_{2n+1}\overset{CH_3}{\underset{*}{\underset{|}{C}H}}-O-\underset{}{\bigcirc}-COCl$ | (p-(1-methylalkyloxy)benzoyl chlorides) |
| $C_nH_{2n+1}\overset{CH_3}{\underset{*}{\underset{|}{C}H}}-O-\underset{}{\bigcirc}-\underset{}{\bigcirc}-COCl$ | (4'-(1-methyl-alkyloxy)-4-biphenylcarboxyl chlorides) |

In the above examples, n represents an integer of 2 to 16, and symbol * represents an optically active carbon; these definitions are applied to subsequent n and *.

The above optically active α-methylalkanoyl chlorides may be prepared according to the following steps:

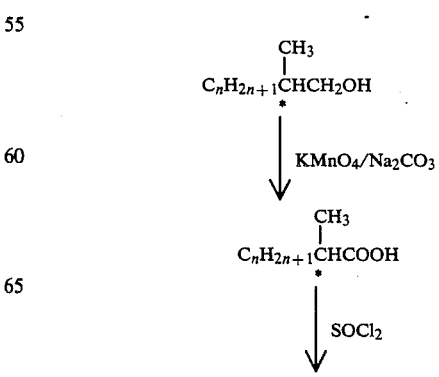

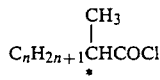

In the above steps, an optically active 2-methylalkanol is oxidized with potassium permanganate to obtain an optically active 2-methylalkanoic acid, which is then reacted with thionyl chloride to prepare an optically active α-methylalkanoyl chloride.

Further, optically active β-methylalkanoyl chlorides may be prepared according to the following steps:

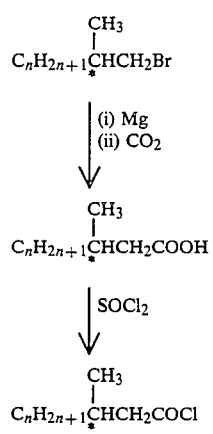

In the above steps, magnesium is reacted with an optically active 1-bromo-2-methylalkane to prepare a Grignard reagent, which is then reacted with dry ice to prepare an optically active β-methylalkanoic acid, which is then reacted with thionyl chloride to prepare an optically active β-methylalkanoyl chloride.

Further, optically active p-(1-methylalkyloxy)benzoyl chlorides and 4'-(1-methyl-alkyloxy)-4-biphenylcarboxyl chlorides may be prepared according to the following steps:

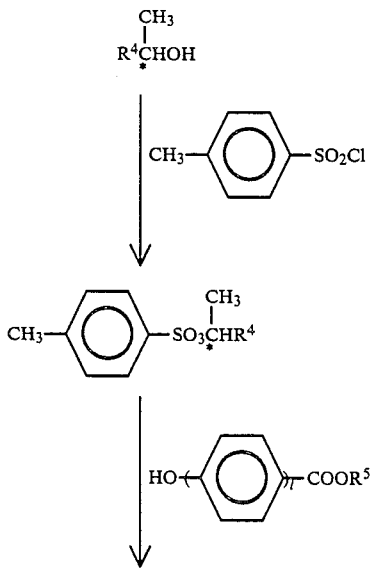

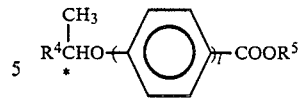

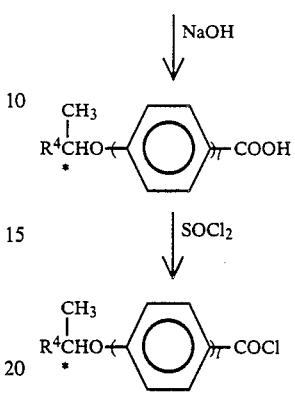

In the above figure, $R^4$ represents an alkyl group having 2 to 16 carbon atoms and $R^5$ represents an alkyl group having a short chain.

In the above steps, an optically active 1-methyl-1-alkanol which is an already known substance is reacted with p-toluenesulfonic acid chloride in the presence of pyridine to obtain a compound (VI), which is then reacted with an alkyl p-hydroxybenzoate or an alkyl 4-hydroxy-4'-biphenylcarboxylate in the presence of KOH to obtain a compound (VII), which is then hydrolyzed in the presence of an aqueous solution of NaOH to obtain a compound (VIII), which is then reacted with thionyl chloride to obtain the objective optically active p-(1-methylalkyloxy)benzoyl chloride or 4'-(1-methylalkyloxy)-4-biphenylcarboxyl chloride (IX).

Further, optically active p-(2-methylalkyl)benzoyl chlorides may be prepared according to the following steps:

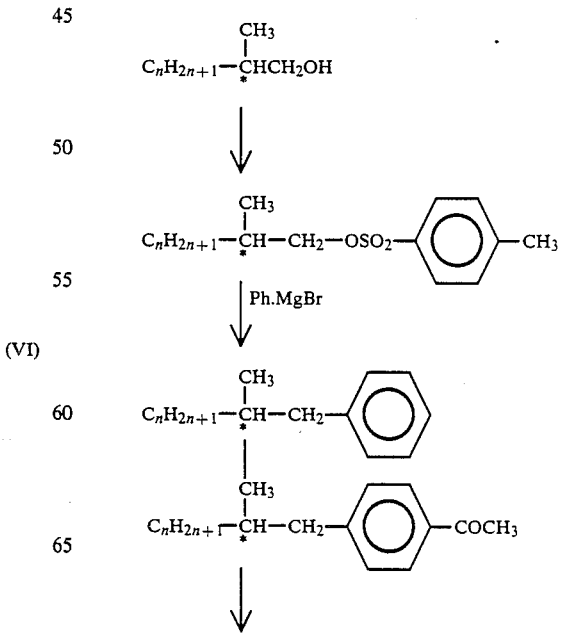

-continued

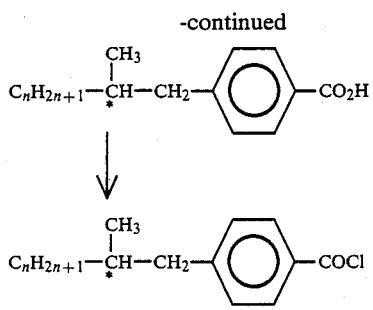

The liquid crystal compounds and liquid crystal compositions of the present invention will be described below in more detail by way of Examples.

EXAMPLE 1

Preparation of 4-n-octyloxy-4'-S-α-methylbutanoyloxybiphenyl (a compound of the formula (III) wherein n=2 and Y=C$_8$H$_{17}$O; i.e. the compound of sample No. 5 of the above Table 2)

(i) Preparation of 4-(acetyloxy)-4'-acetylbiphenyl

4-Hydroxybiphenyl (503.6 g, 2.96 mols) was suspended in 1,2-dichloroethane (2 l), followed by dropwise adding acetyl chloride (278 g, 3.54 mols) to the suspension, heating at 50° C. for 2 hours with stirring to obtain a clear solution, cooling it down to 10° C., portionwise feeding crushed anhydrous aluminum chloride (850 g, 6.37 mols) over one hour, dropwise adding acetyl chloride (278 g, 3.54 mols) over one hour while keeping the temperature at 10°~15° C., stirring at room temperature for 2 hours, further stirring at 50° C. for 2 hours, cooling, pouring the reaction solution in 6N hydrochloric acid (about 3 l), sufficiently stirring, collecting the resulting solids by suction filtering, sufficiently washing with water, drying and recrystallizing from ethanol (3 l) to obtain 4-(acetyloxy)-4'-acetylbiphenyl (581.6 g). Yield: 77.4%. M.P.: 127.5° C.

(ii) Preparation of 4-n-octyloxy-4'-acetylbiphenyl

4-Acetyloxy-4'-acetylbiphenyl (80.0 g, 0.315 mol) was suspended in ethylene glycol monoethyl ether (300 ml), followed by heating with stirring to obtain a uniform solution, pouring a 50% aqueous solution of KOH (70 g) therein, heating under reflux for 30 minutes, dropwise adding 1-bromo-n-octane (62.7 g, 0.325 mol), heating under reflux for 5 hours, cooling with air, pouring the solution on ice (1 l), extracting with toluene (2 l), washing the toluene layer with an acid, then with an alkali aqueous solution, further with water till the washing water became neutral, distilling off toluene for solidification, filtering on heating with toluene (1 l) and active carbon, and recrystallizing to obtain 4-n-octyloxy-4'-acetylbiphenyl (77.5 g). Yield: 75.71%. This product exhibited a smectic B liquid crystal phase (SB), and its C-SB point and SB-I point were 92.5° C. and 132.9° C., respectively.

(iii) Preparation of 4-hydroxy-4'-n-octyloxybiphenyl 4-n-Octyloxy-4'-acetylbiphenyl (38.5 g, 0.119 mol), formic acid (23.8 g, 5.17 mols) and toluene (200 ml) were heated to 60° C., followed by dropwise adding a 35% H$_2$O$_2$ aqueous solution (160.7 g, 1.04 mol) over 1.5 hour while keeping the liquid temperature at 70°~75° C., thereafter heating at 60°~70° C. for 3 hours with stirring, cooling down to room temperature, extracting with toluene (1.5 l), washing with water till the washing water became neutral, drying, removing toluene, adding ethanol (200 ml), heating under reflux, somewhat cooling, adding a 40% NaOH aqueous solution (80 ml), again heating under reflux for 2 hours, pouring the solution in 6N hydrochloric acid (1 l), stirring, collecting the resulting solids by suction filtering, adding toluene (300 ml), withdrawing water and recrystallizing to obtain 4-hydroxy-4'-n-octyloxybiphenyl (18.5 g). Yield: 50.6%. M.P.: 153.6° C.

(iv) Preparation of (+)-S-α-methylbutanoyl chloride

Water (360 ml) was added to S-(−)-2-methyl-1-butanol (167 g), followed by further adding sodium carbonate (41.3 g), stirring at room temperature, dropwise adding potassium permanganate (362 g), dissolved in water (about 8 l) in advance, at 15°~20° C. over 1.5 hour, stirring at room temperature for 6 hours successively heating on a water bath at 45°~55° C. for 2 hours with stirring, suction-filtering, acidifying the filtrate, extracting with toluene (2 l) and distilling under the atmospheric pressure to obtain (+)-S-α-methylbutanoic acid Yield: 78.5 g (38.0%). B.P.: 173°~174° C. [α]$_D^{23}$: (+)17.6.

This product together with thionyl chloride (170 g) were heated under reflux for 4 hours, followed by distilling off excess thionyl chloride under reduced pressure to obtain a raw product, which was then rectified to obtain (+)-S-α-methylbutanoyl chloride. Yield: 75.1 g (86.5%). B.P.: 114°~116° C. [α]$_D^{23}$: (+)17.2.

(v) Preparation of 4-n-octyloxy-4'-S-α-methylbutanoyloxybiphenyl

4-Hydroxy-4'-(n-octyloxy)biphenyl (2.0 g, 6.71 mmols) was dissolved in dry pyridine (15 ml), followed by dropwise adding to the solution a solution (10 ml) of (+)-S-α-methylbutanoyl chloride (0.9 g, 7.47 mmols) prepared in the above (iv) dissolved in dry toluene, sufficiently shaking at room temperature, heating on a water bath at 60° C. for 4 hours, adding toluene (50 ml), washing with an acid, washing with an alkali aqueous solution, washing with water, drying over sodium sulfate, removing toluene, filtering on heating with ethanol (60 ml) and active carbon, and recrystallizing from ethanol (50 ml) to obtain the objective 4-n-octyloxy-4-S-α-methylbutanoyloxybiphenyl (0.8 g). This product exhibited SC* phase and its phase transition points are shown in Table 2, sample No. 5. Further its values of elemental analysis accorded well with its theoretical values as follows:

|   | Analytical values | Theoretical values (in terms of C$_{25}$H$_{35}$O$_3$) |
|---|---|---|
| C | 78.4% | 78.29% |
| H | 9.1% | 9.20% |

Other compounds of the formula (III) in Table 2 were obtained in the same manner as in Example 1.

EXAMPLE 2

Preparation of 4-n-decyloxy-4'-(p-(2-methylbutyl)benzoyloxy)biphenyl (a compound of the formula (IV) wherein m=2, n=2 and Y=n—$C_{10}H_{18}O$; i.e. the compound of Table 3, sample No. 10)

First, 4-hydroxy-4'-n-decyloxybiphenyl was prepared in the same manner as in the case of 4-hydroxy-4'-n-octyloxybiphenyl prepared in Example 1, (i)~(iii).
4-Acetyl-4'-n-decyloxybiphenyl: C-SB point 117.8° C., SB-I point 131.3° C.
4-Hydroxy-4'-n-decyloxybiphenyl: m.p. 149.0° C.

This 4-hydroxy-4'-n-decyloxybiphenyl (0.5 g) was dissolved in dry pyridine (20 ml), followed by dropwise adding to the solution, commercially available (+)-p-(2-methylbutyl)benzoyl chloride (0.4 g), further pouring dry toluene (15 ml) in the mixture, sufficiently shaking at room temperature, further heating on a water bath at 60° C. for 3 hours, cooling down to room temperature, adding toluene (50 ml), twice washing with 6N hydrochloric acid (100 ml), further twice washing with a 2N alkali aqueous solution, several times washing with saturated NaCl aqueous solution to make the liquid neutral, drying over sodium sulfate, distilling off toluene, filtering through active carbon on heating using a mixed solvent of ethanol (20 ml) and ethyl acetate (20 ml), recrystallizing, filtering crystals deposited in a refrigerator, and drying to obtain the objective 4-n-decyloxy-4'-(p-(2-methylbutyl)benzoyloxy)biphenyl (0.3 g). Its phase transition points are shown in Table 3, sample No. 10. Further, its values of elemental analysis accorded well with its theoretical values as follows:

|   | Analytical values | Theoretical values (in terms of $C_{34}H_{44}O$) |
|---|---|---|
| C | 81.7% | 81.56% |
| H | 8.7% | 8.86% |

Other compounds of the formula (iv) in Table 3 were obtained in the same manner as in the case of Example 2.

EXAMPLE 3

Preparation of 4-n-tetradecyloxy-4'-β-methylpentanoyloxybiphenyl (a compound of the formula (II) wherein n=2 and Y=$C_{14}H_{29}O$; i.e. the compound of Table 1, sample No. 3)

(i) Preparation of 4-hydroxy-4'-n-tetradecyloxybiphenyl

4-Hydroxy-4'-n-tetradecyloxybiphenyl was prepared in the same manner as in the case of 4-hydroxy-4'-n-octyloxybiphenyl prepared in Example 1, (i)~(iii).
4-Acetyl-4'-n-tetradecyloxybiphenyl: C-SB point 112.1° C., SB-I point 123.2° C.
4-Hydroxy-4'-n-tetradecyloxybiphenyl: m.p. 144° C.

(ii) Preparation of (+)-S-β-methylpentanoyl chloride

Metal Mg ribbon (12.4 g) was placed in a flask and dried with stirring, followed by cooling, introducing dry ether (50 ml), adding a small amount of ethyl iodide, warming, adding commercially available (−)-S-1-bromo-2-methylbutane (70 g) under cooling, thereafter stirring at room temperature for 1.5 hour, pouring the reaction mixture on crushed dry ice, acidifying with 6N hydrochloric acid, extracting with toluene (200 ml), washing with water, distilling off toluene, heating the residue together with excess thionyl chloride for 3 hours, thereafter distilling off thionyl chloride under reduced pressure and distilling under reduced pressure to obtain (+)-S-β-methylpentanoyl chloride. Yield: 25.3 g (43.6%). B.P.: 197°~198° C. $[\alpha]_D^{29}$: +5.4°.

(iii) Esterification

4-Hydroxy-4'-n-tetradecyloxybiphenyl (0.5 g) prepared in the above (i) was dissolved in dry pyridine (20 ml), followed by dropwise adding to the solution, (+)-S-β-methylpentanoyl chloride (0.2 g) prepared in the above (ii), further pouring dry toluene (15 ml), sufficiently shaking at room temperature, further heating on a water bath at 60° C. for 3 hours, cooling to room temperature, adding toluene (50 ml), twice washing with 6N hydrochloric acid (100 ml), further twice washing with a 2N alkali aqueous solution, several times washing with saturated NaCl aqueous solution to make the liquid neutral, drying over sodium sulfate, distilling off toluene, filtering on heating with ethanol (40 ml) and recrystallizing to obtain the objective (S)-4-tetradecyloxy-4'-β-methylpentanoyloxybiphenyl (0.2 g). Its phase transition points are shown in Table 1, sample No. 3. Further its values of elemental analysis accorded well with its theoretical values as follows:

|   | Analytical values | Theoretical values (in terms of $C_{40}H_{48}O_3$) |
|---|---|---|
| C | 83.5% | 83.28% |
| H | 8.2% | 8.39% |

Other compounds of the formula (III) in Table 1 were prepared as in Example 3.

EXAMPLE 4

Preparation of optically active 4'-(1-methyl-heptyloxy)-4-biphenylcarboxylic acid p-octyloxyphenyl ester (a compound of the formula (V) wherein l=2, m=1, n=6 and Y=—$OC_8H_{17}$; i.e. the compound of Table 4, sample No. 18)

S(+)-2-octanol (200 g, 1.536 mol) was dissolved in dry pyridine (600 ml), followed by dropwise adding a solution of p-toluenesulfonic acid chloride (292.8 g, 1.536 mol) dissolved in dry toluene (440 ml) while the temperature in the system was kept at 10° C. or lower, stirring at room temperature for one hour after completion of the addition, raising the temperature in the system to 50° C., keeping this temperature for 2 hours, cooling, further adding water (1 l) and toluene (500 ml), stirring, washing the separated toluene layer with 6N-HCl, then with a 2N-NaOH aqueous solution, further washing with water till the washing water became neutral, and distilling off toluene to obtain as a residue, optically active p-toluenesulfonic acid 1-methyl-heptyl ester (321.0 g).

On the other hand, 4-hydroxy-4'-biphenylcarboxylic acid ethyl ester (38.7 g, 0.160 mol) was dissolved in ethanol (200 ml), followed by further adding and dissolving KOH (9 g, 0.160 mol), adding optically active p-toluenesulfonic acid 1-methyl-heptyl ester obtained above (50 g, 0.176 mol), keeping the mixture under reflux for 4 hours, cooling, adding toluene (200 ml) and 6N-HCl (50 ml), washing the toluene layer with a 2N-NaOH aqueous solution, washing with water till the washing water became neutral, and distilling off toluene to obtain as a residue, optically active 4'-(1-methyl-heptyloxy)-4-biphenylcarboxylic acid ethyl ester (38.6 g, 0.109 mol), which was dissolved in ethanol (6 ml), NaOH (5.3 g, 0.130 mol) and water (26 ml), following by heating the solution under reflux for 10 minutes to deposit crystals, cooling, adding 6N-HCl (20 ml), separating crystals by filtering, and recrystallizing from acetic acid to obtain optically active 4'-(1-methyl-heptyloxy)-4-biphenylcarboxylic acid (23.4 g). This product exhibited liquid crystal phases and its phase transition points, C-SC* point, SC*-Ch point and Ch-I point were 160° C., 177° C. and 196° C., respectively.

Thionyl chloride (11.3 g, 0.095 mol) was added to the above optically active 4'-(1-methyl-heptyloxy)-4-biphenylcarboxylic acid (20 g, 0.063 mol), followed by heating under reflux for one hour and distilling off excess thionyl chloride to obtain optically active 4'-(1-methyl-heptyloxy)-4-biphenylcarboxylic acid chloride (21 g).

This product (2.0 g, 0.006 mol) was added to a solution of p-octyloxyphenol (1.6 g, 0.007 mol) dissolved in pyridine (5 ml) and the mixture was reacted, followed by heating with stirring, allowing to stand overnight, adding toluene (30 ml) and water (20 ml), stirring, washing the toluene layer with 6N-HCl, then with 2N-NaOH aqueous solution, further with water till the washing water became neutral, distilling off toluene and recrystallizing from ethanol to obtain the objective optically active 4'-(1-methyl-heptyloxy)-4-biphenylcarboxylic acid p-octyloxyphenyl ester (1.6 g). Its phase transition points, C-SC* point, SC*-Ch point and Ch-I point were 78.7° C., 103.3° C. and 120.8° C., respectively. Further its specific angle of rotation $[\alpha]_D^{20}$ was +2.2° (C=0.1 in chloroform). The absolute steric configuration of this substance could not have yet been determined, but since it is considered that Walden inversion might occur at the stage of etherification with the above optically active toluenesulfonate, the absolute steric configuration is presumed to be of R system. Further its values of elemental analysis accorded well with its calculated values as follows:

|   | Analytical values | Calculated values (in terms of $C_{35}H_{46}O_4$) |
|---|---|---|
| C | 79.0% | 79.2% |
| H | 8.2% | 8.74% |

When p-octyloxyphenol used at the final stage in Example 4 was replaced by other phenols, other compounds of the formula (V) shown in Table 4, sample Nos. 13~23, were obtained in the same manner as in Example 4. Their respective phase transition points are shown in Table 4 together with the results of Example 4.

EXAMPLE 5

Preparation of optically active p-(1-methylbutyloxy)benzoic acid 4'-octyloxy-4-biphenylyl ester (a compound of the formula (V) wherein l=1, m=2, n=3 and Y=—OC$_8$H$_{17}$; i.e. the compound of Table 4, sample No. 26)

S(+)-2-pentanol (163.4 g, 1.854 mol) was dissolved in dry pyridine (740 ml), followed by dropwise adding a solution of p-toluenesulfonic acid chloride (353 g, 1.852 mol) dissolved in dry toluene (524 ml) while keeping the temperature in the system at 10° C. or lower, stirring at room temperature for one hour after completion of the addition, raising the temperature in the system to 50° C., keeping the temperature for 2 hours, cooling, further adding water (1 l) and toluene (600 ml), stirring, washing the separated toluene layer with 6N-HCl, then with 2N-NaOH aqueous solution, further with water till the washing water became neutral, and distilling off toluene to obtian as a residue, optically active p-toluenesulfonic acid 1-methyl-butyl ester (413.9 g).

On the other hand, p-hydroxybenzoic acid methyl ester (28.5 g, 0.187 mol) was dissolved in methanol (120 ml), followed by adding and dissolving KOH (10.1 g, 0.187 mol), adding to the solution, optically active p-toluenesulfonic acid 1-methyl-butyl ester obtained above (50 g, 0.206 mol), keeping the mixture under reflux for 4 hours, cooling, adding toluene (200 ml) and 6N-HCl (50 ml), washing the toluene layer with 2N-NaOH aqueous solution, then with water till the washing water became neutral, and distilling off toluene to obtain as a residue, optically active p-(1-methyl-butyloxy)benzoic acid methyl ester (16.6 g, 0.070 mol), which was then dissolved in ethanol (5 ml), NaOH (4.2 g, 0.105 mol) and water (21 ml), heating under reflux for one hour, cooling, pouring the reaction solution in 6N-HCl aqueous solution (50 ml) with stirring, separating deposited crystals by filtration, and recrystallizing from ethanol to obtain optically active p-(1-methyl-butyloxy)benzoic acid having a m.p. of 67.0°~68.8° C. (9.3 g). To this product (6.5 g, 0.031 mol) was added thionyl chloride (6.0 g, 0.047 mol), followed by heating under reflux for one hour and distilling off excess thionyl chloride to obtain optically active p-(1-methyl-butyloxy)benzoic acid chloride (6.2 g).

This product (1 g, 0.004 mol) was added to and reacted with a solution of 4-(4'-octyloxyphenyl)phenol (1.3 g, 0.004 mol) dissolved in pyridine (10 ml), followed by heating with stirring, allowing to stand overnight, adding toluene (30 ml) and water (20 ml), stirring, washing the toluene layer with 6N-HCl, then with 2N-NaOH aqueous solution, further with water till the washing water became neutral, distilling off toluene and recrystallizing the residue from ethanol to obtain the objective optically active p-(1-methyl-butyloxy)-4'-octyloxy-4-biphenylyl ester (1.0 g). Its phase transition points, C-SC* point, SC*-CH point and Ch-I point were 92.0° C., 95.2° C. and 137.0° C., respectively. Further its values of elemental analysis accorded well with its calculated values as follows:

|   | Analytical values | Calculated values (in terms of $C_{32}H_{40}O_4$) |
|---|---|---|
| C | 78.0% | 78.65% |
| H | 8.4% | 8.25% |

When 4-(4'-octyloxyphenyl)phenol used at the final stage in Example 5 was replaced by other phenols, other compounds of the formula (V), i.e. the compounds of Table 4, sample Nos. 24~38 were obtained in the same manner as in Example 5. Their respective phase transition points are shown in Table 4 together with the results of Example 5.

EXAMPLE 6 (USE EXAMPLE 1)

A composition consisting of a compound expressed by the chemical formula

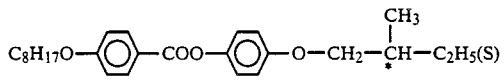

wherein * represents an optically active carbon and (S) represents a steric configuration, (80% by weight), and compounds of sample Nos. 6 and 1 of the present invention (each 10% by weight) exhibits SC* phase up to 44° C., exhibits SA phase at temperatures exceeding 44° C. and becomes an isotropic liquid at 69° C.

This composition was filled in a cell equipped with transparent electrodes having PVA applied thereonto and subjected to parallel aligning treatment by surface-rubbing, and gradually cooled till SC* phase was obtained, while a direct current voltage of 50 V was impressed, to obtain a uniform monodomain cell. When this liquid crystal cell was placed between two pieces of polarizers arranged in a crossed Nicol state, and an alternating current of a low frequency of 15 V and 0.5 Hz, then a clear switching operation was observed and a liquid crystal display element having a very good contrast and a high response rate (2 msec.) was obtained.

In addition, the value of spontaneous polarization of this liquid crystal composition (Ps) was 4.5 nC/cm$^2$.

EXAMPLE 7 (USE EXAMPLE 2)

A composition consisting of compounds of sample Nos. 5, 7, 2 and 3 of the present invention (each 20% by weight) and compounds of sample Nos. 10 and 24 of the present invention (each 10% by weight) exhibits SC* phase up to 86° C., exhibits SA phase at temperatures exceeding 86° C. and becomes an isotropic liquid at 101° C.

To this composition was added an anthraquinone dyestuff, D-16 (made by BDH company) in 3% by weight to prepare the so-called guest-host type composition. When this was filled in a cell similar to that in Example 1, a piece of a polarizer was arranged so that the polarization plane might be perpendicular to the molecular axis and an alternating current of a low frequency of 0.5 Hz and 15 V was impressed, a clear switching operation was observed and a color liquid crystal display element having a good contrast and a high response rate (2 msec.) was obtained.

In addition, the value of spontaneous polarization of this liquid crystal composition (Ps) was 3.6 nC/cm$^2$.

EXAMPLE 8 (USE EXAMPLE 3)

A composition consisting of a compound expressed by the chemical formula

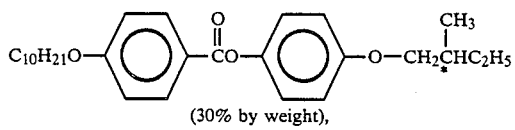

(30% by weight), a compound expressed by the chemical formula

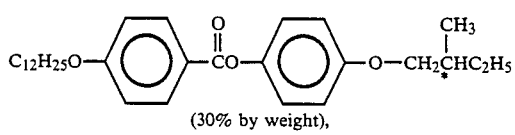

(30% by weight), and the compound of sample No. 16 of the present invention (40% by weight) exhibits SC* phase up to 60° C., exhibits SA phase at temperatures exceeding 60° C. and becomes an isotropic liquid at 87° C.

When an anthraquinone dyestuff, D-16 (made by BDH company) was added in an amount of 3% to the above liquid crystal composition to obtain the so-called guest-host type composition, which was then filled in a cell equipped with transparent electrodes subjected to parallel aligning treatment, one piece of a polarizer was arranged so that the polarization plane might be parallel to the molecular axis, and an alternating current of a low frequency of 0.5 Hz and 15 V was impressed, then a clear switching operation was observed, and a color liquid crystal display element having a very good contrast and a response rate as very high as 1 msec.

In addition, the value of spontaneous polarization of this liquid crystal composition was as very large as 20 nC/cm$^2$.

EXAMPLE 9 (USE EXAMPLE 4)

A composition consisting of compounds of sample Nos. 13, 23, 16 and 17 of the present invention (all in equal amounts) exhibits SC* phase up to 83° C., exhibits SA phase up to 100° C., exhibits Ch phase at temperatures exceeding 100° C. and becomes an isotropic liquid at 105° C.

When this liquid crystal composition was filled in a cell similar to that in Example 6, the composition was placed between two pieces of polarizers arranged in a crossed Nicol state and an alternating current of a low frequency of 0.5 Hz and 15 V was impressed, then a clear switching operation was observed and a liquid crystal display element having a very good contrast and a response rate as very high as 0.2 msec. was obtained.

In addition, this liquid crystal composition exhibited a value of spontaneous polarization as very large as 117 nC/cm$^2$.

EXAMPLE 10 (USE EXAMPLE 5)

The compound of sample No. 18 of the present invention (30% by weight) was added to a liquid crystal composition consisting of the following three liquid crystal compounds, all having a smectic C phase (SC phase) exhibiting no ferroelectric properties:

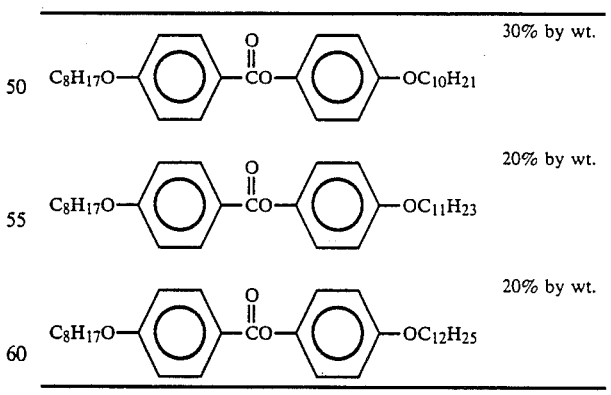

The resulting liquid crystal composition exhibits SC* phase up to 83° C., exhibits Ch phase at temperatures exceeding 83° C. and becomes an isotropic liquid at 96° C.

To this composition was added a dyestuff as in Example 7 to obtain a guest-host composition, one piece of a polarizer was arranged so that the polarization plane might be parallel to the molecular axis; and an alternating current of a low frequency of 0.5 Hz and 15 V was impressed. As a result, a clear switching operation was observed and a color liquid crystal display element exhibiting a very good contrast and a response rate as very high as 2 msec. was obtained. In addition, this liquid crystal composition exhibited a value of spontaneous polarization of 14 nC/cm².

As seen from the above, when a compound expressed by the formula (V) of the present invention is added in about 30% by weight to SC liquid crystal compounds exhibiting no ferroelectric properties, it is possible to obtain a fully practical ferroelectric liquid crystal composition.

EXAMPLE 11 (USE EXAMPLE 6)

A nematic liquid crystal composition consisting of
4-ethyl-4'-cyanobiphenyl: 20% by weight,
4-pentyl-4'-cyanobiphenyl: 40% by weight,
4-octyloxy-4'-cyanobiphenyl: 25% by weight, and
4-pentyl-4'-cyanoterphenyl: 15% by weight,
was filled in a cell equipped with transparent electrodes having polyvinyl alcohol (PVA) applied and subjected to a parallel aligning treatment by surface-rubbing (distance between the electrodes; 10 μm) to prepare a TN type display cell, which was observed under a polarization microscope. As a result, a reverse domain was observed to be formed.

To the above nematic liquid crystal composition was added the compound of sample No. 9 of the present invention in 0.1% by weight. A TN cell was similarly prepared from the resulting composition and observed. As a result, the reverse domain was dissolved and a uniform nematic phase was observed.

Further, even when the above compound of sample No. 9 was replaced by that of sample No. 22 and a composition obtained by adding this compound in 0.1% by weight was used, the same effectiveness was obtained.

What we claim is:

1. A liquid crystalline ester compound expressed by the formula (I)

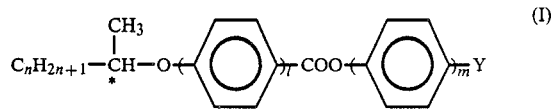

wherein n is an integer of from 2 to 8; l is 1 or 2 and m is 1 or 2 under the condition that l+m=3; Y represents R, OR, —OCOOR or —COOR wherein R throughout represents an alkyl group of 4 to 14 carbon atoms; and the asterisk shows an optically active carbon atom.

2. A compound of claim 1, expressed by the following formula (Va)

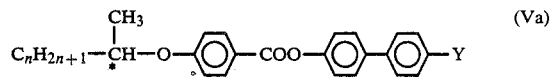

wherein n and Y each are as defined in claim 1.

3. A compound of claim 1, expressed by the formula (Vb)

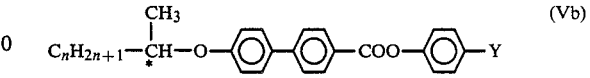

wherein n and Y each are as defined in claim 1.

4. A chiral smectic liquid crystal composition of at least two components containing at least one compound of claim 1.

5. A chiral smectic liquid crystal composition consisting only of a plurality of compounds of claim 1.

* * * * *